United States Patent [19]

O'Lenick, Jr.

[11] Patent Number: 5,446,183
[45] Date of Patent: Aug. 29, 1995

[54] SILICONE ESTER EMULSIFIERS

[75] Inventor: Anthony J. O'Lenick, Jr., Lilburn, Ga.

[73] Assignee: Siltech Inc., Norcross, Ga.

[21] Appl. No.: 389,138

[22] Filed: Feb. 15, 1995

[51] Int. Cl.⁶ .......................... C07F 7/08; C07F 7/18
[52] U.S. Cl. .................................. 556/437; 556/440
[58] Field of Search .............................. 532/440, 437

[56] References Cited

U.S. PATENT DOCUMENTS

| 3,511,699 | 5/1970 | Sterman . | |
|---|---|---|---|
| 3,560,544 | 2/1971 | Haluska | 556/440 |
| 4,937,277 | 6/1990 | O'Lenick, Jr. | 556/437 X |
| 5,136,063 | 8/1992 | O'Lenick, Jr. | 556/440 X |
| 5,196,499 | 3/1993 | O'Lenick, Jr. | 556/437 X |
| 5,248,783 | 9/1993 | O'Lenick | 556/437 X |
| 5,296,625 | 3/1994 | O'Lenick, Jr. . | |
| 5,374,759 | 12/1994 | Imperante et al. | 556/437 |
| 5,401,871 | 3/1995 | Feldmann-Crane et al. | 556/437 X |

Primary Examiner—Paul F. Shaver

[57] ABSTRACT

The invention discloses novel ester emulsifiers. Compounds of the invention are made by reacting (a) a carboxy silicone, and (b) a fatty alcohol alkoxylate containing 4 to 20 carbon atoms. The compounds of the invention by virtue of (i) the silicone group, (ii) the fatty alcohol group and (iii) the polyoxyalkylene present in the compound are extremely efficient emulsifiers for a variety of oils at heretofore unknown levels.

20 Claims, No Drawings

SILICONE ESTER EMULSIFIERS

BACKGROUND OF THE INVENTION

1. Field of the Invention

The invention discloses novel ester emulsifiers. Compounds of the invention are made by reacting (a) a carboxy silicone, and (b) a fatty alcohol alkoxylate containing 4 to 20 carbon atoms. The compounds of the invention by virtue of (a) the silicone group, (b) the fatty alcohol group and (c) the polyoxyalkylene present in the compound are extremely efficient emulsifiers for a variety of oils at heretofore unknown levels.

The esterification by which the compounds are prepared is the reaction of a carboxy silicone, which may contain varying amounts of polyoxyalkylene in the molecule, and a fatty alcohol alkoxylate.

2. Arts and Practices

Silicone compounds have been known to be active at the surface of plastic, cellulosic and synthetic fibers as well as paper. They are good nondurable lubricants and are very stable to oxidation, however, their high cost and lack of efficiency at low concentrations as well as low durability have made their acceptance in commercial products quite low. In all instances, commercially available quaternaries are the active ingredient in traditional laundry care markets, with little or no silicone added.

The low efficiency and low durability of dimethylpolysiloxane is due to the fact that it is very water insoluble and deposits on the surface to obtain a minimum free energy in the solution. Simply, the silicone oil delivery to the surface by hydrophobic binding, not chemical bonding. At the surface, the dimethylpolysiloxane is a very effective fiber lubricant, however, there are two drawbacks, first; the dimethylpolysiloxane is not chemically bonded so the effect is very transient and disappears with one washing, and second; since there is no reaction of the dimethylpolysiloxane to the surface an equilibrium between fiber absorbed dimethylpolysiloxane and dimethylpolysiloxane in the dispersion results in very inefficient percentage of silicone deposited. A large amount of the expensive silicone goes down the drain with the waste water.

In many applications, there is a strong desire to obtain a solid wax which can be used in applications were a spread on application is of interest. These applications include personal care applications like antiperspirants and skin creams. Unfortunately most silicone derivatives are liquid to very low temperatures. Attempts to overcome this deficiency have been made by reacting stearyl alcohol with a chlorosilane. The difficulty with the use of this type of material is that a large excess (50% by weight) of the alcohol needs to be added to get a product which is free of the irritating chlorosilane raw material, When such an excess is used the product behaves functionally more like the stearyl alcohol than like a silicone compound. Additionally, the compound is not polymeric, hence the superior lubrication and hydrophobicity enhancements which can be achieved by dimethylpolysiloxane is not obtainable with these compounds.

U.S. Pat. No. 3,511,699 to Sterman issued May 12, 1970 teaches that epoxy compounds placed in the silicone backbone by hydrosilation can be cured onto certain fibers to give improved substantivity. The substantivity is based upon the reaction of hydroxyl groups on the cellulosic and the epoxy group in the silicone polymer. The resulting bond is a ether linkage and a new hydroxyl group. While a definite improvement over other compounds the efficiency and durability of the were not good enough to allow for cost effective incorporation of these materials in detergent formulations.

U.S. Pat. No. 5,296,625 to O'Lenick teaches the preparation of the carboxy silicone polymers which are raw materials useful in the reparation of the compounds of the present invention. This patent is incorporated hereinby reference.

THE INVENTION

Object of the Invention

It is the object of the present invention to provide emulsifiers which are effective at very low concentrations. These emulsifiers are effective for making emulsions of various oily materials including but not limited to triglycerides, silicone oil, mineral oil and fatty esters. The formation of oil in water emulsions results in the placing of the oil in a micelle. The concentration of emulsifier needed to make a micelle stable is an important variable in the ability to deliver the oil to a substrate being tested. For example, if it is the desire to deliver silicone oil to a textile substrate from aqueous emulsion, it is desirable to deliver as much of the oil from the micelle efficiently to the surface. The greater the concentration Of emulsifier, the greater the micelle will resist delivering the oil contained therein. The undelivered oil in the emulsion goes down the drain, and is wasted. It is therefore very desirable to develop an emulsifier which gives stable emulsions but is present in minimal concentration so as to allow for through and efficient delivery of the oil to the substrate being treated. The compounds of the present invention are such compounds. They are effective emulsifiers at concentrations as low as 0.05%

The incorporation of the fatty alcohol alkoxylate into the ester results in the improved the efficient emulsification.

SUMMARY OF THE INVENTION

The present invention relates to novel fatty alcohol alkoxylate containing silicone ester compounds. Compounds of the invention by virtue of (a) the ester group, (b) the fatty alcohol alkoxylate groups and (c) the polyoxyalkylene portion of the molecule present in the carboxy silicone are extremely efficient emulsifiers for a variety of oils. The emulsions give a good pay off when applied to substrate, that is they efficiently deliver the oil from the micelle, allowing the oil to spread out when applied to a variety of substrates including hair, skin, wood, plastic and textile fibers. The compounds of the present invention are prepared by reacting a carboxy silicone compound with a fatty alcohol alkoxylate.

The compounds of this invention are made by the esterification of a carboxy silicone compound and a fatty alcohol alkoxylate. Specifically, the compounds of the present invention are esters compounds which is prepared by the esterification reaction of;

(a) a silicone carboxylate conforming to the following structure:

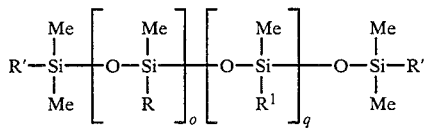

wherein;

Me is methyl;

R and R' are $CH_3$ or $-(CH_2)_3-O-(EO)_a-(PO)_b-(EO)_c-C(O)-R''-C(O)-OH$; with the proviso that both R and R' are not $CH_3$;

R'' is selected from $-CH_2-CH_2-$; $-CH=CH-$; $-CH_2-C(R^7)-H$;

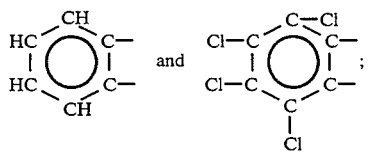

$R^7$ is alkyl having from 1 to 20 carbon atoms;

$R^1$ is selected from lower alkyl $CH_3(CH)_n-$ or phenyl;

n is an integer from 0 to 8;

a, b and c are integers independently ranging from 0 to 20;

EO is an ethylene oxide residue $-(CH_2CH_2-O)-$;

PO is a propylene oxide residue $-(CH_2CH(CH_3)-O)-$;

o is an integer ranging from 1 to 100;

q is an integer ranging from 0 to 500.

and (c) a fatty alcohol alkoxylate conforming to the following structure;

$$CH_3-(CH_2)_n-(CH_2CH_2O)_x-CH_2CH(CH_3)O)_y-(CH_2CH_2O)_z-OH$$

n is ranges from 3 to 19;

x, y and z are independently integers ranging from 0 to 20.

The carboxy silicone compounds useful as raw materials in the preparation of the compounds of the present invention are disclosed in U.S. Pat. No. 5,296,625 to O'Lenick, Jr. et al, incorporated hereinby reference.

The compounds of the present invention conform to the following structure:

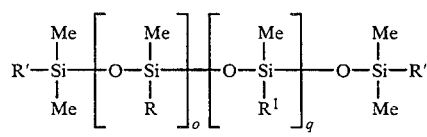

wherein;

Me is methyl;

R and R' are $CH_3$ or $-(CH_2)_3-O-(EO)_a-(PO)_b-(EO)_c-C(O)-R''-C(O)-R_2$; with the proviso that both R and R' are not $CH_3$;

R'' is selected from $-CH_2-CH_2-$; $-CH=CH-$; $-CH_2-C(R^7)-H$;

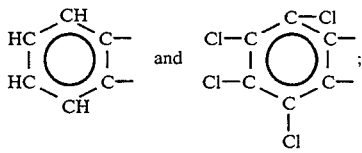

$R^7$ is alkyl having from 1 to 20 carbon atom;

$R^1$ is selected from lower alkyl $CH_3(CH)_n-$ or phenyl;

n is an integer from 0 to 8;

a, b and c are integers independently ranging from 0 to 20;

EO is an ethylene oxide residue $-(CH_2CH_2-O)-$;

PO is a propylene oxide residue $-(CH_2CH(CH_3)-O)-$;

o is an integer ranging from 1 to 100;

q is an integer ranging from 0 to 500;

$R^2$ is $CH_3-(CH_2)_n-(CH_2CH_2O)_x-CH_2CH(CH_3)O)_y-(CH_2CH_2O)_z-o-$;

n is ranges from 3 to 19;

x, y and z are independently integers ranging from 0 to 20.

REFERRED EMBODIMENTS

In another preferred embodiment x+y+z is greater than zero.

In another preferred embodiment n ranges from 3 to 11.

In another preferred embodiment n is 3.
In another preferred embodiment n is 5.
In another preferred embodiment n is 7.
In another preferred embodiment n is 9.
In another preferred embodiment n is 11.
In another preferred embodiment n is 13.
In another preferred embodiment n is 15.
In another preferred embodiment n is 17.
In another preferred embodiment n is 19.

In an especially preferred embodiment, two fatty alcohols having differing n, x, y and z values are blended and reacted with the other reactants. The selection of the blended fatty alcohols allows for the synthesis of extremely effective emulsifiers. The concentrations at which these emulsifiers are effective is heretofore unknown.

In this especially preferred embodiment the compounds of this invention are made by the esterification of a carboxy silicone, and a blend of fatty alcohol alkoxylate. Specifically, the compounds of the present invention are prepared by the esterification reaction of;

(a) a silicone carboxylate conforming to the following structure:

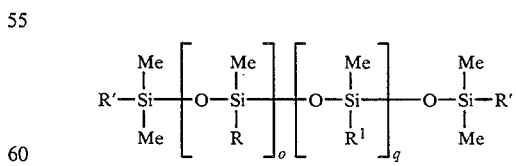

wherein;

Me is methyl;

R and R' are $CH_3$ or $-(CH_2)_3-O-(EO)_a-(PO)_b-(EO)_c-C(O)-R''-C(O)-OH$; with the proviso that both R and R' are not $CH_3$;

R'' is selected from $-CH_2-CH_2-$; $-CH=CH-$; $-CH_2-C(R^7)-H$;

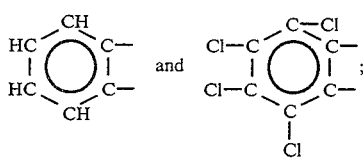

$R^7$ is alkyl having from 1 to 20 carbon atoms;
$R^1$ is selected from lower alkyl $CH_3(CH)_n$— or phenyl;
n is an integer from 0 to 8;
a, b and c are integers independently ranging from 0 to 20;
EO is an ethylene oxide residue —$(CH_2CH_2-O)$—;
PO is a propylene oxide residue —$(CH_2CH(CH_3)-O)$—;
o is an integer ranging from 1 to 100;
q is an integer ranging from 0 to 500.
and (c) a blend of fatty alcohol alkoxylates conforming to the following structures;

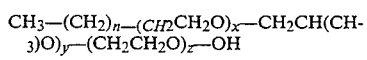

n is ranges from 3 to 19;
x, y and z are independently integers ranging from 0 to 20;

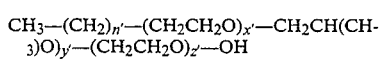

n' is ranges from 3 to 19;
x', y' and z' are independently integers ranging from 0 to 20; with the proviso that
n', x', y' and z' are not all the same as n, y, y, and z.

EXAMPLES

The compounds of the present invention are prepared by the reaction of a carboxy silicone compound and a fatty alcohol alkoxylate. Examples of suitable reactants are as follows;

Reactants

Fatty Alcohol Alkoxylates

Fatty alcohol alkoxylates are commercially available from a variety of suppliers, one supplier is Ethox Chemical of Spartanburg S.C. Fatty Alcohol alkoxylates conform to the following structure;

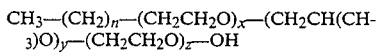

n is ranges from 3 to 19;
x, y and z are independently integers ranging from 0 to 20;

| Reactant Example Number | n Value | x Value | y Value | z Value |
|---|---|---|---|---|
| 1 | 3 | 0 | 0 | 0 |
| 2 | 7 | 10 | 10 | 10 |
| 3 | 9 | 10 | 5 | 0 |
| 4 | 11 | 0 | 15 | 0 |
| 5 | 13 | 10 | 5 | 10 |
| 6 | 15 | 20 | 20 | 20 |
| 7 | 17 | 0 | 0 | 5 |
| 8 | 19 | 20 | 0 | 0 |

Dimethicone Carboxylate Compounds

Dimethicone Carboxylate compounds are disclosed in U.S. Pat. No. 5,296,625 incorporated hereinby reference. They marketed by Siltech under the Silube trade name. The compounds conform to the following generic structure;

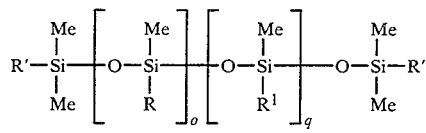

wherein;
Me is methyl;
R and R' are $CH_3$ or —$(CH_2)_3$—O—$(EO)_a$—$(PO)_b$—$(EO)_c$—C(O)—R''—C(O)—OH; with the proviso that both R and R' are not $CH_3$;
R'' is selected from —$CH_2$—$CH_2$—; —CH=CH—; —$CH_2$—C($R^7$)—H;

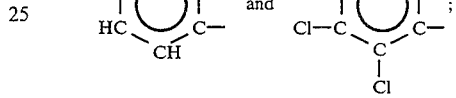

$R^7$ is alkyl having from 1 to 20 carbon atoms;
$R^1$ is selected from lower alkyl $CH_3(CH)_n$— or phenyl;
n is an integer from 0 to 8;
a, b and c are integers independently ranging from 0 to 20;
EO is an ethylene oxide residue —$(CH_2CH_2-O)$—;
PO is a propylene oxide residue —$(CH_2CH(CH_3)-O)$—;
o is an integer ranging from 1 to 100;
q is an integer ranging from 0 to 500.

The carboxy reactants are defined in O'Lenick U.S. Pat. No. 5,296,625 incorporated herein by reference, examples 15-32.

R'' Definition

I) O'Lenick Reactant Example I (Succinic Anhydride)

R'' is —$H_2C$—$CH_2$—

II) O'Lenick Reactant Example II (Alkyl Succinic Anhydride)

R'' is —$(CH_3)$—C—$CH_2$—
\
H

II) O'Lenick Reactant Example III (Alkyl Succinic Anhydride)

R'' is —$(C_{12}H_{25})$—C—$CH_2$—
|
H

IV) O'Lenick Reactant Example IV (Alkyl Succinic Anhydride)

R'' is —$(C_6H_{13})$—C—$CH_2$
\
H

V) O'Lenick Reactant Example V (Alkyl Succinic Anhydride)

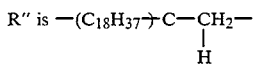

VI) O'Lenick Reactant Example VI (Alkyl Succinic Anhydride)

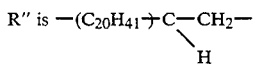

VII) O'Lenick Reactant Example VII (Maleic Anhydride)

R" is —CH=CH—

VIII) O'Lenick Reactant Example VIII (Phthalic Anhydride)

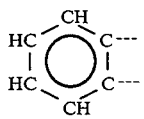

IX) O'Lenick Reactant Example IX R" is (Tetrachlorophthalic anhydride)

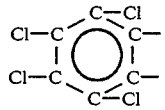

Compounds of the Present Invention

General Reaction Conditions

The esterification can be run without catalyst; however, when no catalysts used reaction rates are less efficient. Standard esterification catalysts are generally used at concentrations of between 0.05% to 0.50% with a preferred range of 0.1% to 0.3%. Catalysts which are effective include but are not limited to; sulfuric acid, p-toluene sulfonic acid, methane sulfonic acid, tin metal, zinc metal, titanium metal, organo titianates, organo tin compounds, organo zinc compounds, zinc oxide, magnesium oxide, calcium oxide, etc.. The most preferred catalyst is stannous oxylate. The reaction is conducted at between 140 and 240 C. under an inert nitrogen blanket. The nitrogen blanket preserves the color. Preferred temperature range is between 180 and 210 C. Water is removed from the reaction which is done using a nitrogen sparge or vacuum.

Examples 33–50

General Procedure

Into a suitable round bottom, three neck flask equipped with a Dean Stark trap, a thermometer and a nitrogen sparge is added the specified number of grams of the carboxy silicone and the specified number of grams of fatty alcohol alkoxylate and 0.25% of total weight of the batch of catalyst. The reaction mass is blanketed with nitrogen, and heated to 180 and 200 C. under an inert nitrogen blanket. Once the reaction temperature reaches 120 C. water begins to boil off and is collected in the Dean Stark Trap. Within four to five hours the theoretical water is collected off and the acid value is very low. The product is used without additional purification.

Example 33

Into a suitable round bottom, three neck flask equipped with a Dean Stark trap, a thermometer and a nitrogen sparge is added the specified number of grams of the carboxy silicone), 74.0 grams of Reactant Example 1, (the fatty alcohol alkoxylate) and 0.25% of total weight of the batch of catalyst. The reaction mass is blanketed with nitrogen, and heated to 180 and 200 C. under an inert nitrogen blanket. Once the reaction temperature reaches 120 C. water begins to boil off and is collected in the Dean Stark Trap. Within four to five hours the theoretical water is collected off and the acid value is very low. The product is used without additional purification.

Example 34–50

Example 33 is repeated only this time substituting the specified number of grams of the specified carboxy silicone for the carboxy silicone specified and the specified type and the specified type and number of grams of fatty alcohol alkoxylate compound as shown below;

Note; In the below table Gms. is grams

| | Carboxy Silicone Compound | | | Fatty Alkoxylate | |
|---|---|---|---|---|---|
| Example | R" Definition | O'Lenick Example | Grams | Example | Grams |
| 33 | I | 15 | 2,429.0 | 1 | 74 |
| 34 | II | 16 | 2,147.0 | 2 | 1600 |
| 35 | III | 17 | 5,398.0 | 3 | 893 |
| 36 | IV | 18 | 533.0 | 4 | 1071 |
| 37 | V | 19 | 4,723.0 | 5 | 1363 |
| 38 | VI | 20 | 3,083.0 | 6 | 3182 |
| 39 | VII | 21 | 3,648.8 | 7 | 490 |
| 40 | VIII | 22 | 1,722.4 | 8 | 1178 |
| 41 | IX | 23 | 1,288.0 | 1 | 74 |
| 42 | I | 24 | 6,100.0 | 2 | 1600 |
| 43 | II | 25 | 10,115.0 | 3 | 893 |
| 44 | III | 26 | 50,269.0 | 4 | 1071 |
| 45 | IV | 27 | 86,185.0 | 5 | 1363 |
| 46 | V | 28 | 2,6450 | 6 | 3183 |
| 47 | VI | 29 | 2,372.0 | 7 | 490 |
| 48 | VII | 30 | 5,229.0 | 8 | 1178 |
| 49 | VIII | 31 | 495.6 | 1 | 74 |
| 50 | IX | 32 | 4,695.0 | 2 | 1600 |

In a preferred embodiment, two fatty alcohols having differing n, x, y and z values are blended and reacted with the other reactants. The selection of the blended fatty alcohols allows for the synthesis of extremely effective emulsifiers. The concentrations at which these emulsifiers are effective is heretofore unknown.

It should be clearly understood, from the teaching of this invention, that the blending of the alcohols prior to the reaction to form the ester results in a single molecule containing both fatty alcohol alkoxylates. The blending of the pre-formed esters of single alkoxylates results in a blend of single substituted esters which do not emulsify as effectively as the ester made from the blended alcohols. This unexpected property of the compounds of the present invention results in unique emulsification properties.

Example 51

Into a suitable round bottom, three neck flask equipped with a Dean Stark trap, a thermometer and a nitrogen sparge is added the specified number grams of the specified carboxy silicone and specified number of grams of two different fatty alcohol alkoxylates and 0.25% of total weight of the batch of catalyst. The reaction mass is blanketed with nitrogen, and heated to 180 and 200 C. under an inert nitrogen blanket. Once the reaction temperature reaches 120 C. water begins to boil off and is collected in the Dean Stark Trap. Within four to five hours the theoretical water is collected off and the acid value is very low. The product is used without additional purification.

Example 51-68

Example 50 is repeated only this time substituting the specified number of grams of the specified carboxy silicone and the specified type and number of grams of the two specified different fatty alcohol alkoxylate compound as shown below;

|  | Carboxy Silicone Compound | | | Fatty Alkoxylate | |
|---|---|---|---|---|---|
|  | R'' | O'Lenick | | | |
| Example | Definition | Example | Grams | Example | Grams |
| 51 | I | 15 | 2,429.0 | 1 | 36 |
|  |  |  |  | 2 | 800 |
| 52 | II | 16 | 2,147.0 | 2 | 800 |
|  |  |  |  | 3 | 446 |
| 53 | III | 17 | 5,398.0 | 3 | 446 |
|  |  |  |  | 4 | 536 |
| 54 | IV | 18 | 533.0 | 4 | 536 |
|  |  |  |  | 5 | 682 |
| 55 | V | 19 | 4,723.0 | 5 | 682 |
|  |  |  |  | 6 | 1641 |
| 56 | VI | 20 | 3,083.0 | 6 | 1641 |
|  |  |  |  | 7 | 245 |
| 57 | VII | 21 | 3,648.8 | 7 | 245 |
|  |  |  |  | 8 | 589 |
| 58 | VIII | 22 | 1,722.4 | 8 | 589 |
|  |  |  |  | 1 | 36 |
| 59 | IX | 23 | 1,288.0 | 1 | 36 |
|  |  |  |  | 8 | 589 |
| 60 | I | 24 | 6,100.0 | 2 | 800 |
|  |  |  |  | 7 | 245 |
| 61 | II | 25 | 10,115.0 | 3 | 446 |
|  |  |  |  | 6 | 1641 |
| 62 | III | 26 | 50,269.0 | 4 | 536 |
|  |  |  |  | 5 | 682 |
| 63 | IV | 27 | 86,185.0 | 5 | 682 |
|  |  |  |  | 1 | 36 |
| 64 | V | 28 | 2,6450 | 6 | 1641 |
|  |  |  |  | 8 | 589 |
| 65 | VI | 29 | 2,372.0 | 7 | 245 |
|  |  |  |  | 5 | 682 |
| 66 | VII | 30 | 5,229.0 | 8 | 589 |
|  |  |  |  | 5 | 682 |
| 67 | VIII | 31 | 495.6 | 1 | 36 |
|  |  |  |  | 3 | 446 |
| 68 | IX | 32 | 4,695.0 | 2 | 800 |
|  |  |  |  | 4 | 536 |

The emulsifiers of the present invention were evaluated as emulsifiers for 60,000 viscosity poly dimethyl siloxane. The formula evaluated was:

| Grams | Material |
|---|---|
| 50.0 | 60,000 viscosity dimethylpolysiloxane |
| 50.0 | Water |

The minimum quantity of emulsifier which gave a stable emulsion was recorder. The lower the number the better the products emulsification properties. The results were as follows:

Prior Art

Fatty Alcohol ethoxylate (non-silicone)
  $CH_3-(CH_2)_{17}-(CH_2CH_2-O)_{11}-H$ 1.8 Grams needed to emulsify
Compounds of the present invention (Single Alcohol)
  Example 62 0.5 grams needed to emulsify
Preferred Compounds of the Present Invention (Alcohol Blends)
  Example 60 0.3 grams needed to emulsify

What is claimed;

1. A compound conforming to the following structure:

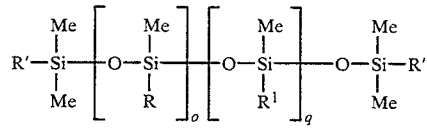

wherein;

Me is methyl;

R and R' are $CH_3$ or $-(CH_2)_3-O-(EO)_a-(PO)_b-(EO)_c-C(O)-R''-C(O)-R_2$; with the proviso that both R and R' are not $CH_3$;

R'' is selected from $-CH_2-CH_2-$; $-CH=CH-$; $-CH_2-C(R^7)-H$;

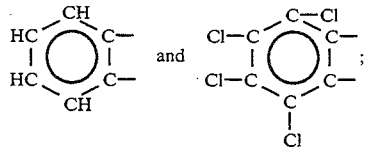

$R^7$ is alkyl having from 1 to 20 carbon atoms;

$R^1$ is selected from lower alkyl $CH_3(CH)_n-$ or phenyl;

n is an integer from 0 to 8;

a, b and c are integers independently ranging from 0 to 20;

EO is an ethylene oxide residue $-(CH_2CH_2-O)-$;

PO is a propylene oxide residue $-(CH_2CH(CH_3)-O)-$;

o is an integer ranging from 1 to 100;

q is an integer ranging from 0 to 500;

$R^2$ is $CH_3-(CH_2)_n-(CH_2CH_2O)_x-CH_2CH(CH_3)O)_y-(CH_2CH_2O)_z-O-$;

n is ranges from 3 to 19;

x, y and z are independently integers ranging from 0 to 20.

2. A compound of claim 1 wherein x+y+z is greater than zero.

3. A compound of claim 1 wherein n ranges from 3 to 11.

4. A compound of claim 1 wherein n is 3.

5. A compound of claim 1 wherein n is 5.

6. A compound of claim 1 wherein n is 7.

7. A compound of claim 1 wherein n is 9.

8. A compound of claim 1 wherein n is 11.

9. A compound of claim 1 wherein n is 13.

10. A compound of claim 1 wherein n is 15.

11. A compound of claim 1 wherein n is 17.

12. A compound of claim 1 wherein n is 19.

13. A silicone ester compound which is prepared by the esterification reaction of;

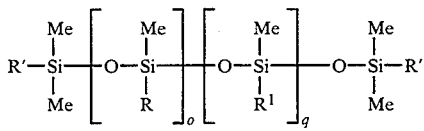

wherein;

Me is methyl;

R and R' are CH₃ or —(CH₂)₃—O—(EO)$_a$—(PO)$_b$—(EO)$_c$—C(O)—R''—C(O)—OH; with the proviso that both R and R' are not CH₃;

R'' is selected from —CH₂—CH₂—; —CH=CH—; —CH₂=C(R)—H;

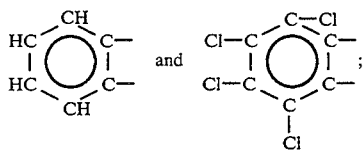

R⁷ is alkyl having from 1 to 20 carbon atoms;
R¹ is selected from lower alkyl CH₃(CH)$_n$— or phenyl;
n is an integer from 0 to 8;
a, b and c are integers independently ranging from 0 to 20;
EO is an ethylene oxide residue —(CH₂CH₂—O)—;
PO is a propylene oxide residue —(CH₂CH(CH₃)—O)—;
o is an integer ranging from 1 to 100;
q is an integer ranging from 0 to 500.

and (c) A blend of fatty alcohol alkoxylates conforming to the following structures;

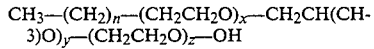

n is ranges from 3 to 19;
x, y and z are independently integers ranging from 0 to 20;

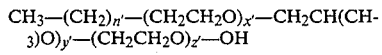

n' is ranges from 3 to 19;
x', y' and z' are independently integers ranging from 0 to 20; with the proviso that n', x', y' and z' are not all the same as n, y, y, and z.

14. A compound of claim 13 wherein x+y+z is greater than zero.
15. A compound of claim 13 wherein n ranges from 3 to 11.
16. A compound of claim 13 wherein n is 3.
17. A compound of claim 13 wherein n is 5.
18. A compound of claim 13 wherein n is 7.
19. A compound of claim 13 wherein n is 9.
20. A compound of claim 13 wherein n is 11.

* * * * *